United States Patent
Braun et al.

(10) Patent No.: US 6,723,874 B1
(45) Date of Patent: Apr. 20, 2004

(54) METHOD OF PRODUCING ACID FLUORIDES FROM ACID CHLORIDES

(75) Inventors: Max Braun, Wedemark (DE); Matthias Rieland, Hannover (DE); Francine Janssens, Vilvoorde (BE); Kerstin Eichholz, Langenhagen (DE); Stefan Palsherm, Barsinghausen (DE)

(73) Assignee: Solvay Fluor und Derivate GmbH, Hannover (DE)

( * ) Notice: Subject to any disclaimer, the term of this patent is extended or adjusted under 35 U.S.C. 154(b) by 0 days.

(21) Appl. No.: 09/856,909

(22) PCT Filed: Nov. 24, 1999

(86) PCT No.: PCT/EP99/09060

§ 371 (c)(1),
(2), (4) Date: May 30, 2001

(87) PCT Pub. No.: WO00/32549

PCT Pub. Date: Jun. 8, 2000

(30) Foreign Application Priority Data

| Nov. 30, 1998 | (DE) | 198 55 252 |
| Jul. 13, 1999 | (DE) | 199 32 554 |
| Sep. 4, 1999 | (DE) | 199 42 374 |

(51) Int. Cl.⁷ ............................................. C07C 51/58
(52) U.S. Cl. ....................................... 562/852; 423/468
(58) Field of Search ......................... 562/852; 423/468

(56) References Cited

U.S. PATENT DOCUMENTS

| 4,003,984 A | * | 1/1977 | Jones et al. |
| 4,372,938 A | | 2/1983 | Oda et al. |
| 5,847,245 A | | 12/1998 | Franz et al. |

FOREIGN PATENT DOCUMENTS

| DE | 2442883 A1 | * | 3/1976 |
| DE | 2460821 A1 | * | 6/1976 |
| DE | 2823969 | | 12/1979 |
| EP | 0005810 | | 12/1979 |
| EP | 0005810 A1 | * | 12/1979 |

OTHER PUBLICATIONS

Franz, Journal of Fluorine Chemistry, vol. 15 (1980) 423–434.*
Woyski, Journal of American Chemistry Society, vol. 72, 1950, pp. 919–921.*
Prakash et al, Journal of Fluorine Chemistry, 56, 1992, pp. 995–997.*
Padma et al, Indian Journal of Chemistry, vol. 20A, 1981, pp. 777–779.*
Franz, Journal of Fluorine Chemistry, vol. 15, 1980, pp 423–434.*
Wolski et al, Journal of American Chemistry Society, vol. 72, 1950, 919–921.*
Prakash et al, Journal of Fluorine Chemistry, 56, 1992, pp995–997.*
Padma et al, Indian Journal of Chemistry, vol. 20A 1981, pp 777–779.*
Franz, Journal of Fluorine Chemistry, vol. 15 (1980) 423–434.*
Woyski, Journal of American Chemistry Society, vol. 72, 1950, pp. 919–921.*
Prakash et al, Journal of Fluorine Chemistry, 56, 1992, pp. 995–997.*
Padma et al, Indian Journal of Chemistry, vol. 20A, 1981, pp. 777–779.*
Jens Chr. Norrild, et al., "A Facile and Efficient Synthesis of (+)–and (−)–allo–Muscarine and Analogs", Short Papers, Mar. 14, 1997.
R. Franz, et al., "Over Trishydrofluride Of Tertiary Amines And Your Employment As Fluorierungsmittel" Journal of Fluorine Chemistry, 15 (1980) 423–434.
R. F. Weinland, et al., "Over hydraulic fluorides of some, partially very weak, organic Basen" Agrikulturchemishces Laboratorium, Oct. 1908.

* cited by examiner

Primary Examiner—Alan L. Rotman
Assistant Examiner—Hector M. Reyes
(74) Attorney, Agent, or Firm—Crowell & Moring LLP

(57) ABSTRACT

Acid fluorides, for example carboxylic acid fluorides and sulfuryl fluoride are produced by reacting the corresponding acid chlorides with hydrogen fluoride adducts of ammonium fluoride or amine hydrofluorides (which act as a catalyst or as a fluorination agent). Consumed HF adducts may be regenerated with HF.

11 Claims, No Drawings

METHOD OF PRODUCING ACID FLUORIDES FROM ACID CHLORIDES

The invention relates to a method of producing acid fluorides from acid chlorides by contacting with hydrogen fluoride adducts of nitrogen-base hydrofluorides.

Acid fluorides, for example carboxylic acid fluorides and sulphuryl fluoride, are advantageous products for use per se or as intermediate products. Sulphuryl fluoride, for example, can be used as a fumigant for vermin, e.g. in wood used in buildings, churches, museums, silos and buildings, and to counteract discolouring enzymes, fungi or pathogens in wood which has not been used for building, e.g. freshly felled wood. Carboxylic acid fluorides are valuable intermediate products in chemical synthesis. Sulphuryl chloride fluoride can be reacted to form sulphuryl fluoride.

German Offenlegungsschrift DE-OS 28 23 969 discloses the preparation of fluorocarbonyl compounds from chlorocarbonyl compounds, for example of chlorodifluoroacetyl fluoride from chlorodifluoroacetyl chloride and HF adducts of hydrofluorides of organic nitrogen bases as fluorination agents. If HF adducts are used, amine is added to bind HF, or solvents having sufficient alkalinity are used to bind HF.

It was an object of the present invention to devise an improved fluorination process for the preparation of acid fluorides from acid chlorides. This object is achieved by the method of the present invention.

The method according to the invention provides for acid fluorides to be prepared from acid chlorides by contacting with hydrogen fluoride adducts of hydrofluorides of organic nitrogen bases or ammonium fluoride. In this case, the method is carried out so that, unlike in the prior art, no base which has an HF-binding effect is added. Nor is any solvent which binds HF used. At best, if in accordance with an embodiment to be described hereafter an acid is added, such as trifluoroacetic acid, this acid or part of this acid may be neutralised by base, by adding a desired quantity of base before, during or after the addition of acid. However, HF is not bound.

In addition to HF adducts of ammonium fluoride, the HF adducts of hydrofluorides of organic nitrogen bases named in German Offenlegungsschrift DE-OS 28 23 969 can be used for contacting. They can be expressed by the formula $B.(HF)_x$, wherein B represents an organic nitrogen base and x is a whole number or a fraction from <1 to 4, preferably 2–3.

Any possible primary, secondary and/or tertiary amines including N-heterocycles may be used as organic nitrogen bases B. If these amines are represented by the formula:

$R_1R_2R_3N$ the meanings therein could be as follows:

| | |
|---|---|
| $R_1$ | an alkyl radical, preferably having 1 to 10, in particular 1 to 6, C atoms, a cycloalkyl radical, preferably having 5 to 7 C atoms, an aralkyl radical, preferably having 6 to 10 C atoms, or an aryl radical, preferably likewise having 6 to 10 C atoms; |
| $R_2$ and $R_3$ | hydrogen, alkyl, cycloalkyl, aralkyl and aryl radicals of the same type as stated under $R_1$. |

The radicals $R_2$ and $R_3$ may be identical or different. Two of the radicals $R_1$ and $R_2$ or $R_3$ may also be closed to form a cycloaliphatic ring, which may optionally be interrupted by other heteroatoms such as oxygen atoms. Likewise, it is possible for the three radicals $R_1$, $R_2$ and $R_3$ to be constituents of a heterocyclic ring, which means that corresponding N-heterocycles then result. Preferred organic nitrogen bases B are primary, secondary and/or tertiary amines having a total of up to 12 C atoms, the secondary and/or tertiary aliphatic amines being particularly preferred.

Concrete examples of the bases B are:

N-butylamine, N-decylamine, diethylamine, di-n-octylamine, trimethylamine, triethylamine, tri-n-propylamine, isopropyl diethylamine, tri-n-butylamine, cyclohexylamine, N-methylaniline, N,N-dimethylaniline, pyrrolidine, piperidine, N-methylpiperidine, morpholine, pyridine, quinoline, etc.

The HF adducts of the hydrofluorides of the nitrogen bases B can easily be obtained from the bases B and hydrogen fluoride; they are low-melting substances, or substances which are liquid at room temperature, with considerable thermal loading ability. The tris-hydrofluorides can even be vacuum-distilled in non-decomposed form.

Preferably HF adducts of primary, secondary or tertiary amine hydrofluorides having up to 15 C atoms are used, in particular secondary and tertiary amine hydrofluorides. HF adducts of tri-n-propylamine hydrofluoride, tri-iso-propylamine hydrofluoride, tri-n-butylamine hydrofluoride, pyridine hydrofluoride, piperidine hydrofluoride or N,N-dimethylamine hydrofluoride are particularly well suited.

The reaction is performed in liquid phase.

The method according to the invention may be performed batchwise or continuously. In the continuous procedure, the procedure may consist of also feeding in HF, fresh HF adduct or both in addition to the acid chloride to be fluorinated. Correspondingly, reaction mixture is separated off or gaseous reaction products are distilled off or removed in gaseous form.

The inventors have discovered that HCl becomes enriched in the reaction mixture over time. If HF is not fed in intermittently or continuously, the reaction mixture or the HF adduct becomes depleted in HF. It has been discovered that the HF adduct can be regenerated by treating with HF, optionally at elevated temperature (80 to 120° C.) and elevated pressure (e.g. autogenous pressure in an autoclave). In so doing, it was shown that it is not necessary completely to expel any HCl present. A residual content of e.g. less than 5% by weight, preferably less than 2% by weight, HCl is acceptable.

According to one embodiment of the invention, sulphuryl fluoride as acid fluoride is prepared from sulphuryl chloride or sulphur dioxide and chlorine (then under pressure for liquefaction). Here, in order to release HCl, an acid is added, for example a halogenated carboxylic acid such as trifluoroacetic acid. A nitrogen base may be added for (partial) neutralisation of this added acid. In that case, this base expediently corresponds to the base contained in the hydrofluoride.

Sulphuryl fluoride may also be prepared from sulphuryl chloride fluoride. Thus two-stage preparation of sulphuryl fluoride is possible. The first stage comprises the preparation of sulphuryl chloride fluoride from sulphuryl chloride. The ratio of amine (or $NH_3$) to HF in the reaction mixture is not limited in this stage; it can also be performed with a very high HF content, e.g. at a ratio of amine to HF of 1:3 up to 1:10 or even above. The second stage, the fluorination of sulphuryl chloride fluoride to sulphuryl fluoride, requires a ratio of amine to HF which is greater than 1:3; for example, it is between 1:2 and 1:3. This proviso in terms of the maximum content of HF in the reaction mixture also applies to one-stage preparation of $SO_2F_2$ from $SO_2Cl_2$, if a good yield of $SO_2F_2$ is to be obtained. It is assumed that for a ratio of amine to HF of less than 1:3 the reactivity (nucleophilic character) of the F⁻ anion changes.

The two-stage preparation of sulphuryl fluoride makes it possible to use a particular method variant, because it has been established that it is simultaneously possible to regenerate the HF adduct (as mentioned above) during the fluorination of $SO_2Cl_2$ to $SO_2ClF$. $SO_2Cl_2$, an excess of HF and HF adduct which is to be regenerated are introduced into a reactor. At elevated pressure (e.g. autogenous pressure in an autoclave), $SO_2ClF$ and regenerated HF adduct are produced simultaneously. Gaseous HCl which forms is separated off (e.g. by letting off the superatmospheric pressure and passing through inert gas such as $N_2$). Then HF is evaporated off, in order to bring the HF content to within the limits described above (amine : HF>1:3). Then the second stage can be performed for the preparation of $SO_2F_2$. If the first and second stages are performed in the same reactor, it is thus possible always to enter the second stage with re-fluorinated HF adduct.

According to another embodiment, carboxylic acid fluorides of Formula I

RC(O)F are prepared in which R stands for C1–C7-alkyl; or for C1–C7-alkyl substituted by at least 1 chlorine atom and/or by at least 1 fluorine atom. Particularly preferably, R stands for C1–C3-alkyl; or for C1–C3-alkyl substituted by at least 1 chlorine atom and/or by at least 1 fluorine atom. Very particularly, R stands for $CH_3$, $C_2H_5$, $CF_3$, $CF_2Cl$, $CFCl_2$, $CCl_3$, $CHF_2$, $C_2F_5$ or $C_3F_7$.

R may however also stand for aromatic radicals such as phenyl or tolyl.

The chlorine-fluorine exchange according to the present invention is preferably performed at a temperature from ambient temperature (about 20° C.) to 150° C. Preferably the molar ratio of the HF adduct of the hydrofluoride, relative to the base contained therein, to acid chloride lies in the range from 1:0.01 to 1:1 (1 mole $R_3N.2.6$ HF and 1 mole acid chloride are then in a ratio of 1:1), if one Cl atom is to be exchanged per acid chloride adduct. In the case of a plurality of chlorine atoms which are to be exchanged per molecule, the use of the hydrofluoride is expediently twice, three times, etc. as high. For a continuous procedure, the ratio may lie in the range from 1:0.01 to 1:100.

Upon the reaction, hydrogen chloride is released spontaneously in the preparation of carboxylic acid fluorides. This hydrogen chloride can be let off from the reactor (for example by a correspondingly adjusted pressure-relief valve). When preparing $SO_2F_2$, the addition of acids such as trifluoroacetic acid is necessary in order to release HCl.

It was established in tests that often the addition of e.g. trifluoroacetic acid right at the beginning of the fluorination reaction is advantageous insofar as the precipitation of solids (which re-dissolve again later) is prevented or reduced. For example, as little as 10 mole % of the acid, relative to the onium-HF adduct calculated as 100 mole %, is sufficient.

It was also established that ammonium salts having three C1 or C2 alkyl radicals very easily release resulting HCl; however, they tend to form solids, so that the addition of e.g. trifluoroacetic acid, as described above, is advantageous. Although onium salts having three C3- or higher-chain alkyl radicals do not form solids, HCl is not so easily released therefrom as from the shorter-chain substituted onium salts.

In this case, addition of acid is advantageous, because this expels HCl more intensively.

According to one embodiment, the hydrofluoride adduct functions as a fluorination agent. It is then used in such a quantity that it is not dehydrofluorinated to such an extent that the stage of the onium monohydrofluoride is exceeded. If, for example, an adduct of the formula $R_3N.2.6$ HF is used, only such a quantity of HF should be used that $R_3N.zHF$ with z=1 or z>1 remains in the reaction mixture. The corresponding hydrochloride should not be produced if it is desired to avoid regeneration under pressure with HF for as long a time as possible. It is sufficient here merely to add HF.

If, for example, a chlorine atom is to be exchanged for a fluorine atom in a compound, at least 1 mole of the adduct $R_3N.2.6$ HF is used per 1.6 moles of the starting compound. If other educts (e.g. $SO_2Cl_2$) or onium salts having a different HF content are used, the stoichiometry should be adapted accordingly.

According to another embodiment, the hydrofluoride adduct functions as a catalyst. Then HF is also introduced into the reaction as fluorination agent. The quantity of HF is then advantageously at least 1 mole HF per chlorine atom to be exchanged. The ratio of the total of free HF and HF bound in the adduct to the chlorine atom to be exchanged may for example lie in the range from about 1:1 up to 1:3, if $SO_2F_2$ is to be prepared from $SO_2Cl_2$ or $SO_2FCl$. In the preparation of carboxylic acid fluorides or $SO_2FCl$, it may be still higher if HF is to act as a solvent. It is also possible to use less than 1 mole HF per chlorine atom to be exchanged; then the HF from the HF adduct which per se has a catalytic effect is consumed, and the yield drops.

Compared with the known method, the hydrofluoride of ammonia or of the organic nitrogen base does not function here as a fluorination agent and reaction partner, but as a catalyst. For this reason, a continuous procedure becomes possible for the first time. The hydrogen chloride released may if desired be let off continuously from the reaction system or be removed upon regeneration. It is not necessary to use a solvent.

Thus the method according to the invention has the advantage that working-up is very much easier: no amine hydrochloride is produced as waste product; and a solvent does not need to be separated off.

A further subject of the invention is a composition which has a fluorinating action. It is obtainable by mixing HF adducts of the formula $B^1.mHF$ and an acid. This has the effect of releasing HCl from the reaction mixture during the preparation of $SO_2F_2$. Optionally, base $B^1$ may also be added, in a quantity less than the quantity necessary to neutralise the acid. $B^1$ stands for $NH_3$ or the base B, as defined above, and m is 1<m<4. The preferred acid is a halogenated carboxylic acid, such as trifluoroacetic acid. The HF adduct of $B^1$ may also be produced in situ. If desired, this acid or part of the acid may be introduced in the form of the salt with $B^1$. The preferred composition has the "formula" $B^1.(0.1-1.0)TFA.(1.0-3.0)HF$. TFA is trifluoroacetic acid. $B^1$ is preferably B. The preferred B is set forth above.

The use of HF adducts of onium salts of nitrogen as fluorination catalyst for the fluorine-chlorine exchange and the fluorine-bromine exchange in carbon atoms activated by additional electronegative substituents, in particular in C(O)Cl and C(O)Br groups, is likewise a subject of the invention.

The following examples are intended to explain the invention further, without limiting its scope. Examples 1 to 6 explain the use of HF adducts as fluorination agents (presumably autocatalytically), and Examples 7 to 8 explain the use as a catalyst.

EXAMPLES

Example 1

Preparation of Chlorodifluoroacetyl Fluoride (CDFAF) From Chlorodifluoroacetyl Chloride (CDFAC) Using Tributylamine.2.6 HF

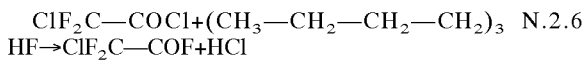

Batch:

| | |
|---|---|
| 0.90 mol chlorodifluoroacetyl chloride (CDFAC) | 134.0 g |
| 0.56 mol tributylamine.2.6 HF | 133.5 g |
| 0.50 mol chlorodifluoroacetic acid | 74.5 g |

Set-up and Performance:

The tributylamine.2.6 HF was placed in a 250 ml three-necked flask with a reflux condenser, temperature sensor and dropping funnel. The reflux condenser was fed with cold brine at a temperature of −20° C. via a cryomat. After the reflux condenser was located a bubble counter, which indicated the escape of gaseous products. In order to collect the reaction product, a 300 ml steel cylinder with dip pipe was connected after the reflux condenser, the cylinder being kept at a temperature of −78° C. in a Dewar flask with $CO_2$/methanol.

CDFAC was then dropped into the solution slowly and with vigorous stirring at room temperature. The reaction was slightly exothermic, with the temperature not increasing to above 31° C. Immediately after dropwise addition had begun, evolution of gas was observed. The first sample was taken after the condenser after 15 minutes. Several samples were taken during the reaction, and after about two-thirds of stoichiometry HCl was also detected in the waste gas stream. After one hour, the cryomat was set to −30° C., because too much CDFAC was escaping. Once the CDFAC had been completely added, stirring was continued until the evolution of gas (bubble counter) was at an end. Then the temperature was raised again to 50° C. in order fully to expel the reaction products in the water bath, until no further escape of reaction products could be detected at the bubble counter. Then the CDFA was added in order to expel HCl completely.

Evaluation

The gas samples at the beginning of the reaction had a content of 91% chlorodifluoroacetyl fluoride and 7% entrained chlorodifluoroacetyl chloride (% GC surface area) and initially no HCl. Once a total of 0.6 mol CDFAC had been introduced dropwise, the resulting HCl was also released from the reaction solution and confirmed using GC-MS. The steel cylinder contained a mixture of 91.7% CDFAF and 6.9% CDFAC entrained from the reaction, as well as 1.4% HCl (owing to the temperature, which was too low for HCl condensation, the resulting HCl was not condensed in the steel cylinder). The isolated yield of CDFAF and CDFAC was 89.5% of theory.

Examples of the Preparation of $SO_2F_2$ from $SO_2Cl_2$ Using Tributylamine.2.6 HF and Tributylamine.TFA.2.6 HF

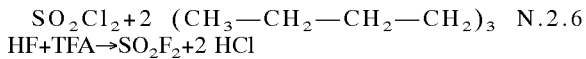

Example 2

Subsequent addition of TFA to release the HCl

Batch:

| | |
|---|---|
| 0.30 mol sulphuryl chloride ($SO_2Cl_2$) | 40.5 g |
| 0.375 mol tributylamine.2.6 HF | 71.2 g |
| 0.375 mol trifluoroacetic acid | 42.8 g |

Set-up and performance from this example also applies to all subsequent examples:

The tributylamine complex was placed in a 250 ml three-necked flask with a reflux condenser, temperature sensor and dropping funnel. The reflux condenser was fed with cold brine at a temperature of −30° C. via a cryomat. A bubble counter installed after the reflux condenser showed that products were leaving via the reflux condenser. In order to collect the reaction product, a steel cylinder (having a volume of approx. 300 ml) with dip pipe and gas outlet was connected after the condenser, the cylinder being kept at a temperature of −78° C. in a Dewar flask with $CO_2$/methanol. $SO_2Cl_2$ was then dropped into the solution slowly and with vigorous stirring at room temperature. The reaction was slightly exothermic. A short time after dropwise addition had begun, evolution of gas was observed, and GC analysis of the gas after the reflux condenser indicated 85.6% $SO_2F_2$ in addition to 14.3% $SO_2FCl$ (no HCl). At the beginning of the reaction, the solution in the flask became somewhat darker in colour, but became light again, and virtually colourless, after some time.

Since hitherto no HCl had been detected in the waste gas (necessary in use for catalytic fluorination), once the evolution of gas from the above reaction was at an end (observation of bubble counter), trifluoroacetic acid (TFA) was added carefully dropwise. Immediately, HCl and also further quantities of $SO_2F_2$ were released from the reaction solution. In order to complete the expulsion of reaction products and the reaction, the reaction solution was brought to 50° C. until no further evolution of gas was observed at the bubble counter. The isolated yield in the cylinder was only 48% owing to the inadequate cooling.

Example 3

Experiment with a TFA/NBu$_3$ ratio of 1:1/Immediate use of Bu$_3$N/HF/TFA as catalyst mixture Batch:

| | |
|---|---|
| 0.23 mol $SO_2Cl_2$ | 31.7 g |
| 0.20 mol tributylamine.2.6 HF | 47.5 g |
| 0.123 mol tributylamine | 22.8 g |
| 0.323 mol trifluoroacetic acid | 36.8 g |

Set-up:

As for Example 2.

Preparation of the fluorinating composition:

The HF adduct of tributylamine and the tributylamine were mixed together. Then the trifluoroacetic acid was added slowly dropwise.

Performance of the fluorination:

The $SO_2Cl_2$ was added slowly dropwise. HCl and also $SO_2F_2$ and $SO_2FCl$ could be detected immediately in the waste gas.

Example 4

Test with NBu$_3$/TFA=1:0.1
Batch:

| | |
|---|---|
| 0.35 mol SO$_2$Cl$_2$ | 47.2 g |
| 0.30 mol tributylamine.2.6 HF | 71.2 g |
| 0.03 mol tributylamine | 5.6 g |
| 0.03 mol trifluoroacetic acid | 3.4 g |

Set-up and performance
As for Example 3.
When the first drops of SO$_2$Cl$_2$ were added, the waste gas had a composition of 73.4% SO$_2$F$_2$ and 25.1% SO$_2$FCl, and initially no HCl. Later, the composition changed somewhat in favour of the sulphuryl fluoride to 97.2% SO$_2$F$_2$ and only 2.0% SO$_2$FCl and 0.3% HCl. A mass balance was not established.

Example 5

Test with NBu$_3$/TFA=1:0.23
Batch:

| | |
|---|---|
| 0.35 mol SO$_2$Cl$_2$ | 47.2 g |
| 0.30 mol tributylamine.2.6 HF | 71.2 g |
| 0.09 mol tributylamine | 16.7 g |
| 0.09 mol trifluoroacetic acid | 10.34 g |

Set-up and performance:
As for Example 3. In this experiment, a suitable steel cylinder was cooled with liquid nitrogen, in order to obtain a mass balance.
When the first drops of SO$_2$Cl$_2$ were added, the waste gas had a composition of 85.1% SO$_2$F$_2$ and 14.8% SO$_2$FCl and 0.6% HCl. The mixture condensed in the steel cylinder consisted of 82% SO$_2$F$_2$ and 18% SO$_2$FCl and traces of HCl and SO$_2$. This corresponds to a theoretical yield of 90.3%, relative to isolated quantities of SO$_2$F$_2$ and SO$_2$FCl.

Example 6

Preparation of trifluoroacetyl fluoride (TFAF) from trifluoroacetyl chloride (TFAC) with tributylamine.2.6 HF as catalyst
Batch:

| | |
|---|---|
| 104.2 g tributylamine.2.6 HF | 0.44 mol |
| 151.0 g trifluoroacetyl chloride | 1.14 mol |

Set-up and performance:
The tributylamine.2.6 HF was placed in a 250 ml multi-necked flask with stirrer, temperature sensor and a condenser placed on top (−50° C.) and a bubble counter at the outlet, and TFAC was introduced with stirring at room temperature.
The reaction became slightly exothermic (T max. 32° C.). Spontaneous evolution of gas occurred. During the reaction, the colour of the solution changed from light to medium brown. Once the experiment had ended, corrosion of the glass was observed in the bottom.
A sample of the waste gas after the bubble counter contained 88.3% TFAF in addition to TFAC and HCl. A mass balance was not established.

Examples 7 and 8

Experiments for the use of NBu$_3$.2.6 HF as fluorination catalyst

Example 7

Continuous process using tributylamine.2.6 HF (without TFA) as catalyst
Batch:

| | |
|---|---|
| 0.74 mol sulphuryl chloride (SO$_2$Cl$_2$) | 100.00 g |
| 0.40 mol tributylamine.2.6 HF | 94.9 g |
| 0.46 mol 1,1,1,3,3-pentafluorobutane (S 365mfc) | 68.3 g |
| 1.48 mol HF | 29.6 g |

Set-up and performance (applies to the subsequent example):

365 and sulphuryl chloride were placed in a 250 ml PFA washing bottle and were cooled with ice. Then HF was introduced carefully with stirring. The tributylamine complex was placed in a 250 ml three-necked flask with a reflux condenser, temperature sensor and dropping funnel. The reflux condenser was fed with cold brine at a temperature of −30° C. via a cryomat. The mixture consisting of HF/S365/SO$_2$Cl$_2$ was dropped into the oily, light-brown solution slowly and with vigorous stirring at room temperature. The reaction was exothermic (ΔT=22° K.), and the internal temperature rose to the boiling point of the 365mfc (41° C.). The 365mfc was retained in the reaction flask by the condenser. A short time after dropwise addition had begun, evolution of gas was observed; in addition to HCl, SO$_2$F$_2$ and mainly SO$_2$FCl were released. A mass balance was not established.

Example 8

Continuous process using tributylamine.2.6 HF with TFA as catalyst

Batch:

| | |
|---|---|
| 0.80 mol sulphuryl chloride (SO$_2$Cl$_2$) | 107.98 g |
| 0.20 mol tributylamine.2.6 HF | 47.74 g |
| 1.60 mol HF | 32.0 g |
| 0.77 mol S 365mfc | 113.3 g |
| 0.02 mol tributylamine | 3.7 g |
| 0.02 mol trifluoroacetic acid | 2.3 g |

Set-up and performance:
See above.
A short time after dropwise addition had begun, evolution of gas was observed; in addition to HCl, SO$_2$F$_2$ and mainly SO$_2$FCl were released. The 365mfc was very largely retained in the reaction flask by the condenser. The evolution of HCl took place somewhat earlier than in the preceding experiment. A mass balance was not established.

Example 9

Use of NEt$_3$.2.6 HF as fluorination catalyst for the preparation of SO$_2$F$_2$ NEt$_3$.2.6 HF+SO$_2$Cl$_2$→SO$_2$F$_2$ Batch:

| Substance | Molecular weight | Weight in g | Moles |
|---|---|---|---|
| Triethylamine.2.6 HF | 153.22 | 58.2 | 0.38 |
| Sulphuryl chloride | 134.97 | 41.6 | 0.31 |

Performance:

Triethylamine.2.6 HF was placed in a three-necked flask with a glass condenser (~0° C.) and final bubble counter, and SO$_2$Cl$_2$ was added dropwise with stirring at room temperature. At the beginning of the dropwise addition of SO$_2$Cl$_2$, the waste gas leaving the condenser had a composition of 63% SO$_2$F$_2$ in addition to 37% SO$_2$FCl. Towards the end of the reaction, the SO$_2$F$_2$ content dropped to 56% SO$_2$F$_2$. A mass balance was not established.

Example 10

Preparation of SO$_2$FCl from SO$_2$Cl$_2$ using tributylamine.4.5 HF

SO$_2$Cl$_2$+(CH$_3$—CH$_2$—CH$_2$—CH$_2$)$_3$N.4.5 HF→SO$_2$FCl+HCl

Batch:

| | | |
|---|---|---|
| 0.24 mol sulphuryl chloride (SO$_2$Cl$_2$) | 47.2 g | |
| 0.24 mol tributylamine.4.5 HF | 68.4 g | |

Set-up and performance:

The tributylamine was placed in a 250 ml three-necked flask with a reflux condenser, with a bubble counter, temperature sensor and dropping funnel. The reflux condenser was fed with cold brine at a temperature of approximately 0° C. via a cryomat. SO$_2$Cl$_2$ was then added dropwise to the oily, light-brown solution slowly and with vigorous stirring at room temperature. The reaction was slightly exothermic (ΔT=10° K.). A short time after dropwise addition had begun, evolution of gas was observed. As a means of monitoring the reaction, gas chromatography samples were taken from the waste gas stream after the bubble counter during the dropwise addition. At the beginning of the addition of SO$_2$Cl$_2$ the waste gas composition was 55.2% HCl, in addition to 42.07% SO$_2$FCl; SO$_2$ was also detected. Once dropwise addition of SO$_2$Cl$_2$ had ended, the waste gas composition was virtually identical. A mass balance was not established.

Example 11

Preparation of acetyl fluoride from acetyl chloride with triethylamine.2.6 HF as catalyst Batch:

| | |
|---|---|
| 61.3 g triethylamine.2.6 HF | 0.40 mol |
| 50.2 g acetyl chloride | 0.64 mol |

Set-up and performance:

The triethylamine complex was placed in a 250 ml three-necked flask with a reflux condenser, temperature sensor and dropping funnel. The reflux condenser was fed with cold brine at a temperature of +15° C. via a cryomat. Acetyl chloride was added dropwise into the oily, light-brown solution slowly and with vigorous stirring at room temperature. The reaction was slightly exothermic, and the evolution of gas took place spontaneously. Once the addition had ended, the solution was heated for 1 hour to 80° C., in order to complete the reaction and to drive out any dissolved acetyl fluoride.

Evaluation:

At the beginning of the addition of acetyl chloride, the waste gas composition was 10.98% HCl, 80.97% acetyl fluoride, 6.59% non-reacted acetyl chloride and 1.46% acetic acid (the latter presumably formed by moisture present in the sampling cylinder; proportions each given in % GC). Once dropwise addition had ended, the waste gas composition was 9.57% HCl, 27.53% acetyl fluoride, 58.01% non-reacted acetyl chloride and 4.89% acetic acid.

Example 12

Preparation of acetyl fluoride from acetyl chloride with tributylamine.4.0 HF as catalyst Batch:

| | |
|---|---|
| 79.6 g tributylamine.4.0 HF | 0.30 mol |
| 70.7 g acetyl chloride | 0.90 mol |

Set-up and performance:

The tributylamine complex was placed in a 250 ml three-necked flask with a reflux condenser (and bubble counter), temperature sensor and dropping funnel. The reflux condenser was fed with cold brine at a temperature of −15° C. via a cryomat. Acetyl chloride was added dropwise into the oily, light-brown solution slowly and with vigorous stirring at room temperature. The reaction was slightly exothermic, and the evolution of gas took place spontaneously. Once the addition had ended, the solution was heated for another hour to 80° C., in order to complete the reaction and to drive out any dissolved acetyl fluoride.

Evaluation:

At the beginning of the addition of acetyl chloride, the waste gas composition was 50.63% HCl, 37.80% acetyl fluoride, 8.15% non-reacted acetyl chloride and 3.43% acetic acid (the latter formed by moisture present in the sampling cylinder; proportions each given in % GC). Once dropwise addition had ended, the waste gas composition was 31.57% HCl, 45.96% acetyl fluoride, 19.98% non-reacted acetyl chloride and 2.50% acetic acid.

Examples 11 and 12 prove that acetyl fluoride can also be prepared with adducts having a relatively high HF content.

Examples 13 to 19 explain the regeneration (recycling) of the HF adduct contaminated by HCl.

Example 13

Recycling of NBu$_3$·1.7 HCl to form NBu$_3$·Y HF using little HF

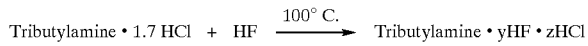
Tributylamine · 1.7 HCl + HF $\xrightarrow{100°\text{C.}}$ Tributylamine · yHF · zHCl Batch:

| Substance | Molecular weight | Weight in g | Moles |
|---|---|---|---|
| Tributylamine·1.7 HCl | 247.34 | 82.17 | 0.33 |
| HF | 20.01 | 50 | 2.5 |

Tributylamine·1.7 HCl was placed in a laboratory autoclave. After closure, 50 g HF was added and the mixture was boiled for approximately 3 hours at 100° C. internal reactor temperature. The autoclave was then cooled to approximately 60° C. internal reactor temperature, and the gas phase up to atmospheric pressure in the autoclave was passed into a washing bottle with water.

Determined according to the chloride and fluoride analysis of the washing bottle, the catalyst remaining in the autoclave then had a composition of tributylamine·0.62 HCl·7.3 HF.

The example shows that even HF adduct which is completely spent, forming hydrochloride, can be regenerated. The regenerated adduct was able to be re-used in fluorination reactions.

The following example shows that the HCl content of this product can be reduced still further.

Example 14

Further reduction of the HCl content in NBu$_3$·0.62 HCl·7.3 HF to form NBu$_3$·Y HF using an excess of HF

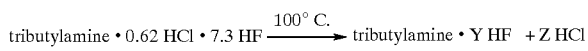
tributylamine · 0.62 HCl · 7.3 HF $\xrightarrow{100°\text{C.}}$ tributylamine · Y HF + Z HCl Batch:

| Substance | Molecular weight | Weight in g | Moles |
|---|---|---|---|
| Tributylamine·0.62 HCl·7.3 HF | 354.3 | 116.83 | 0.33 |
| HF | 20.01 | 107 | 5.35 |

Another 107 g HF was then added to the mixture from Example 13 of tributylamine·0.62 HCl·7.3 HF remaining in the autoclave, and the mixture was boiled overnight at about 100° C. The autoclave was then cooled to approximately 60° C. internal reactor temperature, and the gas phase up to atmospheric pressure in the autoclave was passed into a washing bottle with water. Determined according to the chloride and fluoride analysis of the washing bottle, the catalyst remaining in the autoclave then had a composition of tributylamine·0.005 HCl·4.89 HF. This composition was confirmed by direct analysis of the remaining residue in the autoclave. The HCl had thus been expelled virtually completely. Decomposition products of the amine were not found.

The resulting composition was excellently usable as a fluorination reagent and fluorination catalyst.

Example 15

Recycling of NEt$_3$·1.0 HCl to form NEt$_3$·Y HF using an excess of HF

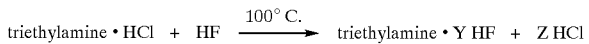
triethylamine · HCl + HF $\xrightarrow{100°\text{C.}}$ triethylamine · Y HF + Z HCl Batch:

| Substance | Molecular weight | Weight in g | Moles |
|---|---|---|---|
| Tributylamine·HCl | 137.65 | 37.93 | 0.28 |
| HF | 20.01 | 107.7 | 5.38 |

Performance:

Triethylamine hydrochloride was placed in a laboratory autoclave, which was closed. Then HF was added and the mixture was boiled overnight at an internal reactor temperature of 100° C. Then at 100° C. reactor temperature the gas phase up to atmospheric pressure was let off into a washing bottle filled with water. Determined according to the chloride and fluoride analysis of the washing bottle, the catalyst remaining in the autoclave then had a composition of triethylamine·0.09 HCl·5.35 HF. This composition was confirmed by direct analysis of the remaining residue in the autoclave. The HCl had thus been expelled virtually completely. Decomposition products of the amine were not found.

Example 16

Adjusting the ratio of amine to HF to 2.8 in the catalyst mixture from Example 15

Performance:

The triethylamine·0.09 HCl·5.35 HF mixture obtained in Experiment 15 was poured into a PFA bottle with frit and the excess HF was expelled with dry nitrogen. Once the weight of the bottle had remained constant for 30 minutes, a vacuum of 10$^{-3}$ mbar was applied for another 10 minutes in order really to remove all the residual amounts of HF. The catalyst thus obtained, according to chloride, fluoride and amine analysis, then had a composition of triethylamine·2.8 HF. HCl could no longer be found. The recyclability of the catalyst was thereby proved.

The adjustment of the amine/HF ratio which was effected reproduced the nucleophilic properties of the adduct. It was then excellently suitable as a reagent for the preparation of SO$_2$F$_2$ from SO$_2$Cl$_2$.

Example 17 and 18

Variation of the duration of the regeneration

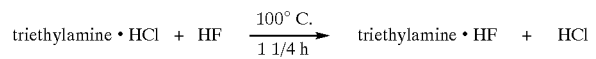

Batch:

| Substance | Molecular weight | Weight in g | Moles |
|---|---|---|---|
| Tributylamine.HCl | 137.65 | 10.00 | 0.07 |
| HF | 20.01 | 16.5 | 0.82 |

Performance:

Triethylamine hydrochloride was placed in a laboratory autoclave, which was closed. Then HF was added and the mixture was boiled for 1¼ hours at a reactor temperature of approximately 100° C. (autoclave was pre-heated for 15 minutes). After this time, the gas phase, within 15 minutes, while the autoclave stood in a oil bath, was let off and analysed (sample 1). The reactor contents (18.07 g) were poured into a PFA bottle and flushed for 5 minutes with nitrogen (18.02 g), 1.54 g of this solution was taken and was made up to 1 liter with distilled water and analysed using a wet chemical process (sample 2).

| | Cl [g/l] | F [g/l] | TEA [g/l] |
|---|---|---|---|
| Sample 1 | 1.80 | 8.49 | 0.07 |
| Sample 2 | 0.02 | 0.80 | 0.74 |

TEA = triethylamine

The analysis data then yielded a catalyst composition of: NEt$_3$.5.75 HF.0.08 HCl

Example 19

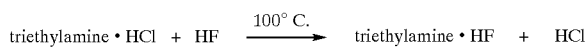

Batch:

| Substance | Molecular weight | Weight in g | Moles |
|---|---|---|---|
| Tributylamine.HCl | 137.65 | 10.44 | 0.08 |
| HF | 20.01 | 21.3 | 1.06 |

Performance:

Triethylamine hydrochloride was placed in a laboratory autoclave, which was closed. Then HF was added and the mixture was boiled for 30 minutes at a reactor temperature of approximately 100° C. (autoclave was pre-heated for 15 minutes). After this time, the autoclave was removed from the oil bath and the gas phase was let off within 15 minutes and analysed (sample 1). The reactor contents (20.96 g) were poured into a PFA bottle and flushed for 5 minutes with nitrogen (20.64 g), 1.1 g of this solution was taken and was made up to 1 liter with distilled water and analysed using ion chromatography (sample 2).

| | Cl [g/l] | F [g/l] | TEA [g/l] |
|---|---|---|---|
| Sample 1 | 2.66 | 1.89 | <0.10 |
| Sample 2 | 0.02 | 0.67 | 0.42 |

The analysis data yielded a catalyst composition of: triethylamine.8.48 HF.0.14 HCl.

What is claimed is:

1. A method of producing an acid fluoride from a corresponding acid chloride, the acid fluoride being selected from the group consisting of sulfuryl fluoride and sulfuryl chloride fluoride, by contacting sulfuryl chloride, sulfuryl chloride fluoride, or sulfur dioxide and chlorine to produce sulfuryl fluoride, or by contacting sulfuryl chloride or sulfur dioxide and chlorine to produce sulfuryl chloride fluoride with a hydrogen fluoride adduct of ammonium hydrofluoride or of a hydrofluoride of an organic nitrogen base, without the addition of an HF-binding base or an HF-binding solvent,
   wherein the hydrogen fluoride adduct serves as a fluorination reagent, and is not dehydrofluorinated beyond the stage of ammonium hydrofluoride or of the hydrofluoride of the organic nitrogen base.

2. A method according to claim 1, characterized in that the method is performed continuously.

3. A method according to claim 1, characterized in that sulfuryl fluoride is prepared from sulfuryl chloride or a mixture of sulfur dioxide and chlorine, the molar ratio of amine or ammonia and HF in the reaction mixture being kept above 1:3.

4. A method according to claim 1 for the preparation of sulfuryl fluoride with regeneration of the HF adduct, wherein in a first stage sulfuryl chloride and HF are reacted together in the presence of the HF adduct which is to be regenerated, with sulfuryl chloride fluoride and regenerated HF adduct being produced, and in a second stage the resulting sulfuryl chloride fluoride is reacted to form sulfuryl fluoride, in the presence of HF adduct, wherein in the second stage the molar ratio of amine or ammonia to HF in the reaction mixture is kept above 1:3.

5. A method according to claim 1, characterized in that the HF adduct of a primary, secondary or tertiary aliphatic amine hydrofluoride with up to 15 C atoms or of a primary, secondary or tertiary amine hydrofluoride with at least one aromatic radical is used.

6. A method according to claim 5, characterized in that the HF adduct of a hydrofluoride of a secondary or tertiary aliphatic amine having a total of up to 15 C atoms or of a secondary or tertiary amine with a phenyl group is used.

7. A method according to claim 6, characterized in that the HF adduct of triethylamine hydrofluoride, tri-n-propylamine hydrofluoride, tri-iso-propylamine hydrofluoride, tri-n-butylamine hydrofluoride, pyridine hydrofluoride, piperidine hydrofluoride or N,N-dimethylamine hydrofluoride is used.

8. A method according to claim 1, wherein the sulfuryl chloride, sulfuryl chloride fluoride, or sulfur dioxide and chlorine is contacted with said hydrogen fluoride adduct at a temperature from ambient temperature to 150° C.

9. A method according to claim 1, further characterized in that an acid is added.

10. A method according to claim 9, wherein the acid is a halocarboxylic acid.

11. A method according to claim 9, wherein the acid is trifluoroacetic acid.

* * * * *